(12) United States Patent
Liu et al.

(10) Patent No.: US 12,343,080 B2
(45) Date of Patent: Jul. 1, 2025

(54) VISION TESTING SYSTEM AND METHOD

(71) Applicant: OcuXcel Corporation, Nepean (CA)

(72) Inventors: Kexing Liu, Nepean (CA); Anirbaan Mukherjee, Behala (IN)

(*) Notice: Subject to any disclaimer, the term of this patent is extended or adjusted under 35 U.S.C. 154(b) by 868 days.

(21) Appl. No.: 17/551,918

(22) Filed: Dec. 15, 2021

(65) Prior Publication Data

US 2022/0192482 A1 Jun. 23, 2022

Related U.S. Application Data

(60) Provisional application No. 63/127,058, filed on Dec. 17, 2020.

(51) Int. Cl.
*A61B 3/024* (2006.01)
*A61B 3/00* (2006.01)
*A61B 3/032* (2006.01)

(52) U.S. Cl.
CPC ............ *A61B 3/024* (2013.01); *A61B 3/0033* (2013.01); *A61B 3/0041* (2013.01); *A61B 3/032* (2013.01)

(58) Field of Classification Search
CPC ..... A61B 3/024; A61B 3/0033; A61B 3/0041; A61B 3/032
See application file for complete search history.

(56) References Cited

U.S. PATENT DOCUMENTS

| | | | |
|---|---|---|---|
| 4,818,091 A | 4/1989 | Sadun et al. | |
| 5,892,570 A | 4/1999 | Stevens | |
| 5,946,075 A | 8/1999 | Horn | |
| 6,578,966 B2 | 6/2003 | Fink et al. | |
| 6,656,131 B2 | 12/2003 | Alster et al. | |
| 6,742,894 B2 | 6/2004 | Stewart | |
| 6,769,770 B2 | 8/2004 | Fink et al. | |
| 7,101,044 B2 | 9/2006 | Fink | |
| 7,220,000 B2 | 5/2007 | Alster et al. | |
| 7,275,830 B2 | 10/2007 | Alster et al. | |
| 7,367,675 B2 | 5/2008 | Maddalena et al. | |
| 7,798,645 B2 | 9/2010 | Roser | |
| 8,047,652 B1 | 11/2011 | Collazo | |
| 8,708,495 B2 | 4/2014 | Kohn et al. | |
| 9,039,182 B2 | 5/2015 | Huang | |
| 9,131,838 B1 * | 9/2015 | Bruun-Jensen | ........ A61B 3/005 |

(Continued)

FOREIGN PATENT DOCUMENTS

DE 102004053629 11/2007

OTHER PUBLICATIONS

Wolfgang Fink, Alfredo A. Sadun, "Three-dimensional computer-automated threshold Amsler grid test," (Jan. 1, 2004), J. Biomed Opt. 9(1), p. 149-153 (Year: 2004).*

*Primary Examiner* — Eric F Winakur
*Assistant Examiner* — Hy Khanh Doan

(57) ABSTRACT

A method and apparatus for generating a visual field pattern which serves as a subjective test protocol to evaluate central vision using dynamic image generation to prevent the brain from filling-in to provide better results of patient feedback and reporting of locations of visual disturbance. This enables effective central vision testing to detect the presence of visual field disruptions including scotoma, visual-neurological perceptual effects such as filling-in, and Troxler fading. The present method and apparatus can be used for vision monitoring and self-assessment, and more particularly for monitoring vision for damage or disease to the macula or retina.

19 Claims, 10 Drawing Sheets

(56) References Cited

U.S. PATENT DOCUMENTS

| | | |
|---|---|---|
| 9,155,461 B2 | 10/2015 | Bartlett et al. |
| 9,629,538 B2 | 4/2017 | Wang |
| 10,251,545 B2 | 4/2019 | Carrafa et al. |
| 10,413,172 B2 | 9/2019 | Jensen et al. |
| 2008/0309879 A1 | 12/2008 | Hirji |
| 2019/0133439 A1* | 5/2019 | Ichikawa ............. A61B 3/0033 |
| 2019/0142270 A1* | 5/2019 | Monhart ................. G06F 3/017 351/209 |
| 2021/0007599 A1 | 1/2021 | Grondin et al. |

* cited by examiner

A          B          C

A          B          C

VISION TESTING SYSTEM AND METHOD

CROSS-REFERENCE TO RELATED APPLICATIONS

This application claims priority to U.S. provisional patent application US63/127,058 filed 17 Dec. 2020, which is hereby incorporated by reference herein in its entirety.

FIELD OF THE INVENTION

The present invention pertains to a central vision testing system and method for the detection of visual blurring and/or distortion. The present invention also pertains to an apparatus and method for central vision testing for the detection of visual damage or disease to the macula region of the eye.

BACKGROUND

The human eye is a complex system whose purpose is to provide an image of the environment to the brain. The front portion of the eye comprising the cornea and crystalline lens projects an image on the back surface of the eye, known as the retina, whose photoreceptor cells detect light and send signals to the brain which interprets them as images. At the very center of the retina is the region called macula which is about 5 mm across in an adult eye or 18 degrees equivalent of field of view. The macula is responsible for all of the central vision, with the fovea at the center of the macula aiding in most of the color vision and the fine details of what one sees. The retina contains millions of light-sensitive rod and cone cells and other nerve cells that receive and organize visual information and send this information to the brain through the optic nerve enabling sight. Therefore, a healthy macula is critical for proper standards of vision.

Damage or disease in retina and macula is common, and can result in blurred or distorted vision, defects in central and/or side vision, and mild to complete loss of vision. Some common examples of retinal disease include macular degeneration, retinitis pigmentosa, diabetic retinopathy, and glaucoma. Age-related macular degeneration (AMD) is a degenerative retinal disease affecting millions of people and is the most common cause of blindness in the aged population. AMD disease is generally one of two types: dry AMD which is a result of atrophy in the layers of retina around the macula; and wet AMD whereby abnormal blood vessels leak fluid and/or blood into the macula. At the time this disclosure is written, there is no cure for AMD disease.

The most common way to manage AMD is through healthy lifestyle and consumption of certain supplements combined with very frequent and regular central vision tests at home for early detection of vision changes, with home-based (supervised or unsupervised) central vision monitoring playing an essential role in managing and monitoring vision disease progression. Testing allows patients to monitor new or existing macular edema, detect new abnormal blood vessels that leak fluid or blood into the macula, identify any new or existing scotomas, and detect atrophic changes in the retina associated with symptomatic changes in vision that may be the result of dry AMD. At the very advanced stage of AMD, primarily the wet AMD, certain medicines may be used as injections via the vitreous body to slow down the growth of the irregular and harmful new blood vessel growth. In tandem with the invasive treatments, daily central vision testing at home is the clinically recommended protocol to timely detect new abnormal blood vessels which may leak fluid or blood into the macula which in turn jeopardizes or worsens central vision.

The most common home-based central vision test is a two-dimensional square grid called an Amsler grid which is printed on a piece of paper or provided in an electronic application on a smartphone or a tablet computing device. Most frequently, the Amsler grid has a white background with black lines making up the boxes and square, with the contrast of the grid increased by using a black background and white lines. The test is completed with one eye at a time and with prescription glasses if the patient normally wears them. The Amsler grid is typically held at a working distance of about 28 to 30 cm away, and the patient is asked to gaze at the dot in the center of the grid while indicating if any part of the lines are missing or wavy. By reporting any visual distortion on the grid the patient can identify the presence of scotomas when any or part of the squares is not visible. Noticeable disturbance in the gridlines can also be used to monitor any presence of macular edema and any form of central retinal atrophic morphosis if the squares do not all look equal or if some of the lines look wavy.

There have been some attempts to digitize forms of the Amsler grid. In one example, U.S. Pat. No. 8,047,652 to Collazo describes a portable electronic device having a touch sensitive display for displaying an electronic Amsler chart and receiving input from the user to capture the portion of said display selected by the user. In another example, U.S. Pat. No. 6,578,966 to Fink describes a computer-based visual field test system and analysis where a visual field test pattern is displayed to the patient on an electronic display device and the patient's responses to the visual field test pattern are recorded. A visual field representation is then generated from the patient's responses.

"Filling-in" is a powerful visual ability of the brain which provides multiple benefits to human vision. The fact that we do not perceive an 'empty' region in our visual field corresponding to the blind spot where the optic nerve meets the retina indicates that our visual system perceptually fills-in the blind spot with the information surrounding it. Similar types of perceptual filling-in have been reported for pathological scotomas. This phenomenon can also be demonstrated when central fixation is maintained over an extended period of time while viewing a target camouflaging a sample area of a static background of uniform contrast or variable texture. Over time, the sample camouflaged area gets filled in with information from the immediate surround and begins to provide an area of "no-vision" that blends into the surrounding region.

Another visual-neurological phenomenon is Troxler's fading, which is an optical illusion affecting visual perception wherein when one fixates on a particular point for even a short period of time, an unchanging stimulus away from the fixation point will fade away and disappear such that a physically present visual stimuli entirely disappears from consciousness. Troxler fading occurs because even if one's eyes drift a little when fixating at a point, in the perception field the movements are not significant enough to observe other elements and the retinal neurons remain focused on the main object with the visual focus while ignoring stimuli from other elements in the periphery. Because the brain is so effective at filling-in visual areas of invariant stimuli, images and visual features can disappear from our awareness. Therefore, areas of early stage scotomas may be missed if they are being filled-in by the brain, which can cause false test results. In particular, effective brain filling-in can cause the test to underreport missing pathological changes in the retina and hinder the effectiveness of using Amsler Grid to identify onset or progress of scotoma. There remains a need for a visual field-based testing protocol that provides an accurate visual field map while addressing and minimizing perceptual filling-in and Troxler fading.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a central vision testing system and method for the detection of visual blurring and/or distortion. Another object of the present invention is to provide an apparatus and method for central vision testing for the detection of visual damage or disease to the macula region of the eye.

In an aspect there is provided a method for vision testing comprising: displaying, on an electronic display device, a testing image comprising a static visual grid, at least one visual reference point, and a dynamic background; positioning a person at a working distance from the electronic display device; dynamically changing at least one of the background color, brightness, shade, and texture at a frequency sufficient to interrupt at least one of the Troxler effect and the filling-in effect; and receiving input for recording location of any perceived visual aberration relative to the visual grid.

In an embodiment, the grid is a square grid, rectangular grid, or bull's eye grid.

In another embodiment, the at least one visual reference point is a central reference in the visual grid.

In another embodiment, the at least one visual reference point is a plurality of dots equidistant from the centre of the grid.

In another embodiment, the electronic display is a touch display, and receiving input for recording is done by touching a location on the visual grid at one or more location of any perceived visual aberrations in the visual grid.

In another embodiment, the visual grid covers a field of view of +/−10 degrees at working distance during the testing.

In another embodiment, at the working distance a peripheral reference dot disappears into the blind spot of the person's eye undergoing testing.

In another embodiment, the method further comprises creating a retina map comprising the location of any perceived visual aberration where the visual aberration is recorded.

In another embodiment, the electronic display device is a computer monitor or a tablet screen.

In another embodiment, the dynamic background changing is cyclical and concentric with the visual grid.

In another embodiment, the dynamic background change has periodicity of less than or equal to 4 seconds.

In another embodiment, the method further comprises using a peripheral reference array for calibrating the working distance.

In another embodiment, the method is used in detecting one or more retinal disease.

In another embodiment, the retinal disease is macular degeneration, diabetic retinopathy, or glaucoma.

In another embodiment, the input for recording is from a mouse, stylus, or finger.

In another embodiment, the background brightness of the testing image is adjustable and can be reduced to a threshold level with respect to the grid to conduct threshold central vision testing.

In another aspect there is provided a vision testing apparatus comprising: a viewing device comprising a visual grid on a transparent viewing screen; a programmable backlighting device behind the viewing screen for backlighting the visual grid to create a dynamically changing background sufficient to interrupt at least one of the Troxler effect and the filling-in effect; and a camera device behind the backlighting device to capture a location of visual aberration as indicated by a user.

In an embodiment of the apparatus, the programmable backlighting device is an LED array is programmed to vary its brightness level repeatedly in an outwardly concentrically pattern to dynamically change the background luminance.

In another embodiment of the apparatus, the camera device tracks movement of a marking device in front of the viewing screen; and the marking device is a laser pointer or a light pen.

In another embodiment, the apparatus further comprises a central reference at the center of the visual grid and at least one peripheral reference.

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION OF THE INVENTION

Figure 1A:
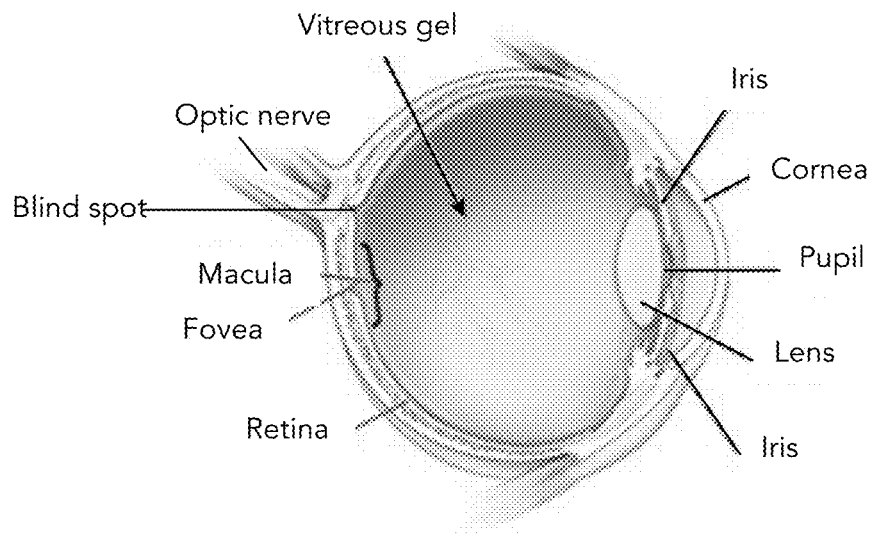
FIG. 1A illustrates the anatomy of the human eye.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

As used herein, the term "about" refers to an approximately +/−10% variation from a given value. It is to be understood that such a variation is always included in any given value provided herein, whether or not it is specifically referred to. The recitation of ranges herein is intended to convey both the ranges and individual values falling within the ranges, to the same place value as the numerals used to denote the range, unless otherwise indicated herein.

The use of any examples or exemplary language, e.g. "such as", "exemplary embodiment", "illustrative embodiment" and "for example" is intended to illustrate or denote aspects, embodiments, variations, elements or features relating to the invention and not intended to limit the scope of the invention.

As used herein, the terms "connect" and "connected" refer to any direct or indirect physical association between elements or features of the present disclosure. Accordingly, these terms may be understood to denote elements or features that are partly or completely contained within one another, attached, coupled, disposed on, joined together, in communication with, operatively associated with, etc., even if there are other elements or features intervening between the elements or features described as being connected.

Herein is provided an apparatus, system, and method which enables effective central vision testing to detect the presence of visual field disruptions including scotoma, while minimizing visual-neurological perceptual effects such as filling-in, and Troxler fading. The present method and apparatus can be used for vision monitoring and self-assessment, and more particularly for monitoring vision for damage or disease to the macula or retina. The invention generates a visual field pattern which serves as a subjective test protocol to evaluate central vision and other visual functions using dynamic image generation to prevent the brain from filling-in to provide better results of patient feedback and reporting of locations of visual disturbance. This provides a highly efficient and inexpensive central visual field test with high result accuracy as well as greatly reduces false negatives by correcting for visual-neurological perceptual effects. Changing the background of the test grid the brain can be inhibited from "filling-in" areas of non-stimulus, thus bypassing Troxler's effect in tandem based on the timings obeyed for the concerned outreach of the retina. By systematic and dynamic image generation during the visual test a retinal disease or damage map can be created to identify relevant damaged or diseased retinal features and/or loci.

Figure 1B:
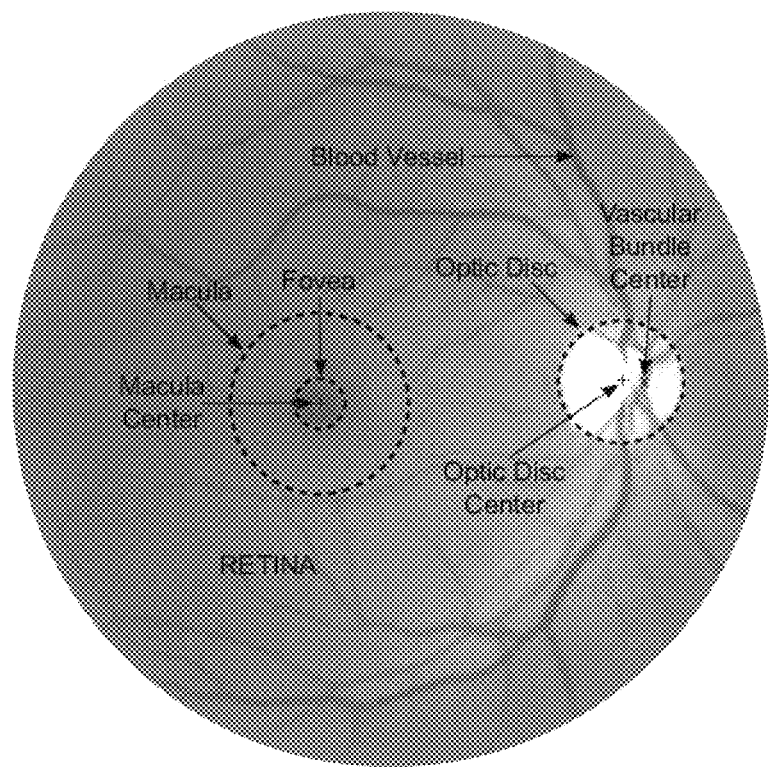
FIG. 1B is a photographic image of a retina identifying the macula and optic disc.

FIG. 1A illustrates the anatomy of the human eye showing the retina and macula. FIG. 1B shows the principal features of a retina. In the center of the retina is the slightly oval-shaped, blood vessel-free reddish spot, the fovea, which is at the center of the area known as the macula. Approximately 17 degrees from the center of the fovea towards the nasal canthus, can be seen the optic nerve, a circular to oval white area measuring about 2×1.5 mm across. From the center of the optic nerve radiates the major blood vessels of the retina. The optic disk is the exit spot of the optic nerve to transfer the processed opto-electric signal to the brain, and is a natural blind spot on the retina as there are no photoreceptor cells at this location.

Figure 2A:
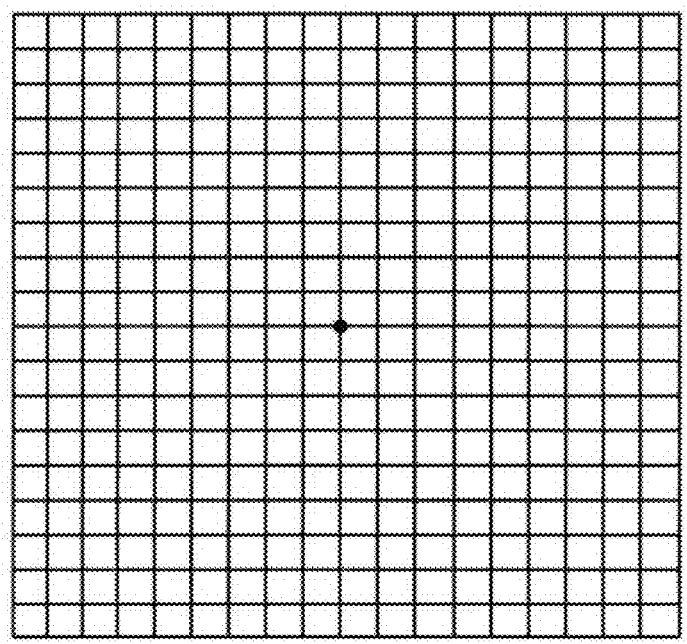
FIG. 2A is a traditional Amsler grid.

FIG. 2A shows a traditional Amsler grid with a centre dot and surrounding square grid with a pattern consisting of a set of evenly distributed lines in both vertical and horizontal directions, appearing as a matrix of perfectly aligned square boxes. The Amsler grid, as a visual grid, is used to test visual field disturbance by regular use and reporting of whether and where lines look wavy or distorted or if areas of the visual field are missing. The Amsler grid, printed on, for example, 8.5"×11" paper, is placed at a consistent distance, preferably between 27-36 cm (10" to 14"), from the eyes. With one eye closed the patient fixes their gaze on the center black dot. The patient tries to keep their gaze fixed and notes if they see grid lines with any discrepancies or aberrations, such as grid lines that are distorted, wavy, or missing, and marks the defect on the chart where new or worsening visual disturbance is indicative of disease or damage progression. This process can be done using a paper grid with a writing implement or on an electronic grid, optionally with a display screen to mark the location of the visual aberration. The test is then complete for the first eye and the patient repeats the test with the other eye. Symptomatic changes in vision due to stages of pathology in the retina lead to visual interpretation of blurring, quenching, missing and distortion of test matrix lines during the test.

Figure 2B:
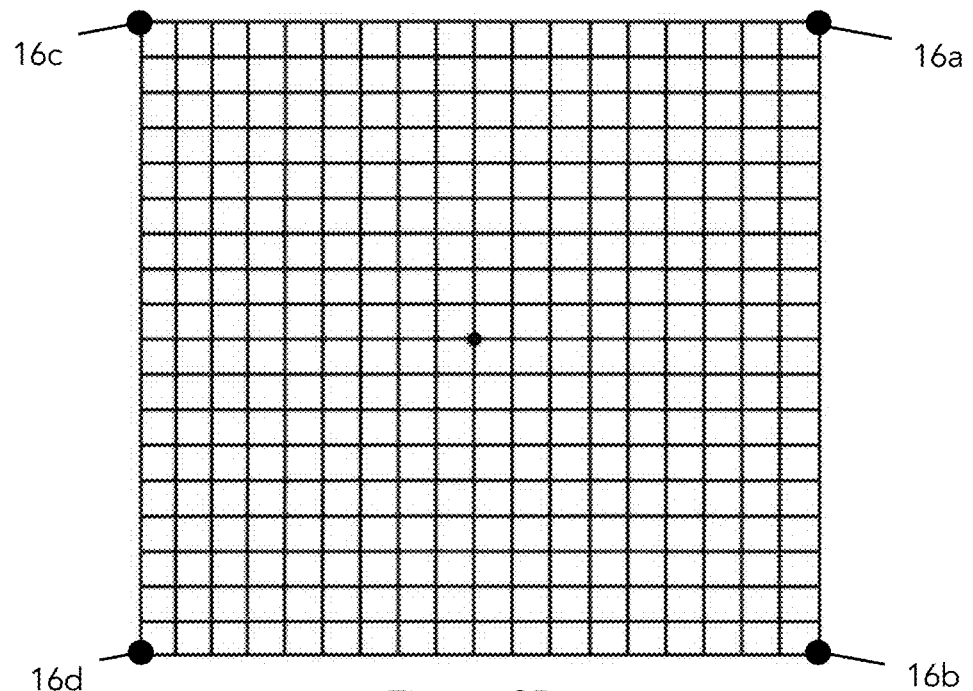
FIG. 2B is a traditional Amsler grid with corner reference dots.

FIG. 2B is a traditional Amsler grid with corner reference dots 16a, 16b, 16c, and 16d. Corner reference dots 16a-d serve as visual reference points and are placed one at each of the four corners of the matrix or visual grid. The replacement corner reference dots can be used as visual reference points as an alternative to the central reference if the patient has severe scotoma in the fovea area and has already lost vision in the very center, such as in the case of severe macular degeneration. In such a case, the patient is not able to fixate gaze at the center and instead can try to look straight into the center by making all four replacement reference dots at the four corners of their peripheral vision visible.

Figure 3A:
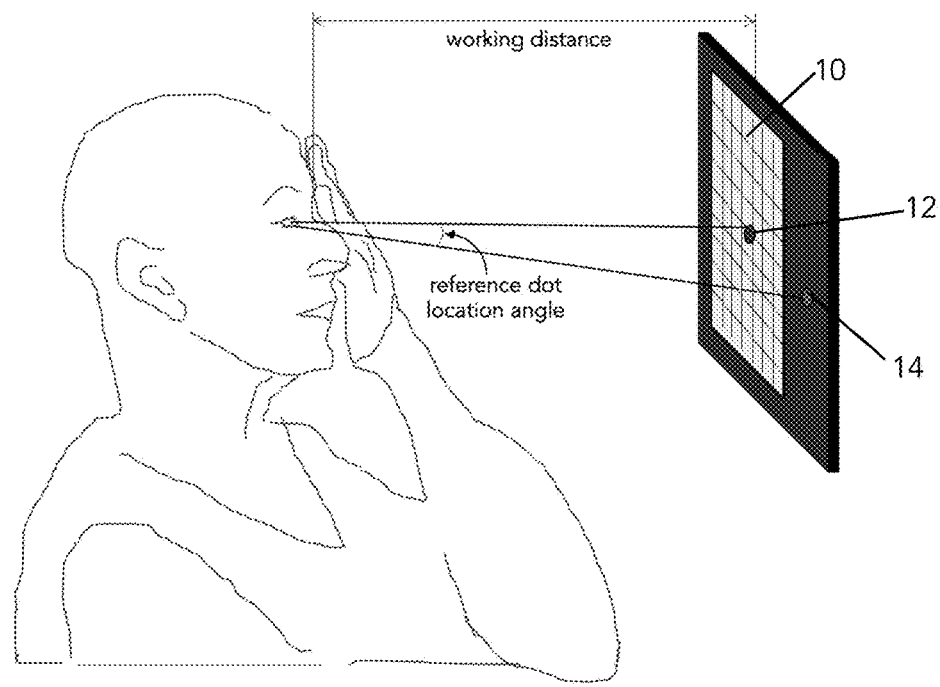
FIG. 3A depicts a person doing a vision test with an Amsler grid.

FIG. 3A depicts a user performing a central vision test with an Amsler grid as an example grid. In the visual grid 10 of the present invention, the central vision testing uses an electronically (digitally) generated visual grid 10 which comprises a regular pattern or matrix, an interior central reference 12 located in the very center of the grid for patient focus, and a dynamically and cyclically changing background behind the grid which fluctuates at a frequency sufficient to interrupt the Troxler effect and filling-in effect. In particular, to avoid the Troxler effect and filling-in effect, movement in the background of the grid during testing prevents filling-in of sections due to undulations in background shades of the grid that can't be ignored because they do not consistently match the surrounding observed regions. Peripheral reference 14 is preferably located along and slightly below the center horizontal line and outside the said matrix to position the electronic display device at a good working distance for the testing.

In one example, the visual matrix is comprised of evenly distributed grid lines in a rectangular matrix. The grid can also be a radial or bull's eye pattern, or can be a regular matrix of lines, dots. The shade of the matrix background is constantly and repetitively changing across the entire visual field of the matrix, hence disrupting the filling-in effect that would normally occur on a static background. In one example bulls-eye style grid the change of degrees or gradients of shade is oriented concentrically, as a result, the area occupied by the visual grid provides a visual effect of cyclically expanding and contracting background shape countering the adaptation at the edges of the possible visual scotomas, thus minimizing occurrence of any perceptual filling-in effect. Digitally generated shades and variation allows fine tuning of the degree of shades and speed of the variation and repetition rate. The change in shade can also be oriented side to side, top to bottom, diagonally, or simply shade patterns that change periodically.

The central reference 12 placed at the very center of the matrix or visual grid provides a central gazing dot for focus of the eye during the test. The central reference 12 can also be replaced with four similar replacement peripheral reference dots, as shown in FIG. 2B, which are placed at each of the four corners of the matrix or visual grid. The replacement reference dots are used if the patient has such severe scotoma in the fovea area that they have already lost significant vision in the very center and are unable to visualize the central reference 12. In such a case, the patient is not able to fixate gaze at the centre of the visual grid 10 and can instead can try to look straight into the center by making all four replacement reference dots at the four corners all visible. A patient examines their eyes one eye at a time by gazing at the central reference 12 dot at the center of the matrix while the background is changing and observe any wavy or missing lines, which is an indication of specific vision impairment or scotoma. The patient can then record any wavy or missing lines in the visual grid that they are able to see by using a stylus or their finger to mark on a touch display screen. Alternatively a camera or motion-sensitive stylus can be used to detect in space the location on the visual grid that the patient is pointing at. A sensor on the screen can locate and record the results.

The recorded test results can then be translated into retinal location and projected onto a retinal map, optional onto an existing fundus retinal image. The electronic device will record the marked area(s), stores in the local device or in the cloud or inter-network storage, and report the finding to a health care provider, and optionally project the findings onto a retina map to indicate the locations on the retina where the scotoma or aberration is recorded. Comparison of past test results chronologically can further provide information on whether the patient's vision is stable or changing, how the vision is changing, and at what rate. The method and ability to collect these remote self-test data allows research, clinical studies, machine learning and artificial intelligence methods to be applied for disease progression modelling, correlation with any specific treatment, provided privacy and security is upheld.

Figure 6A:
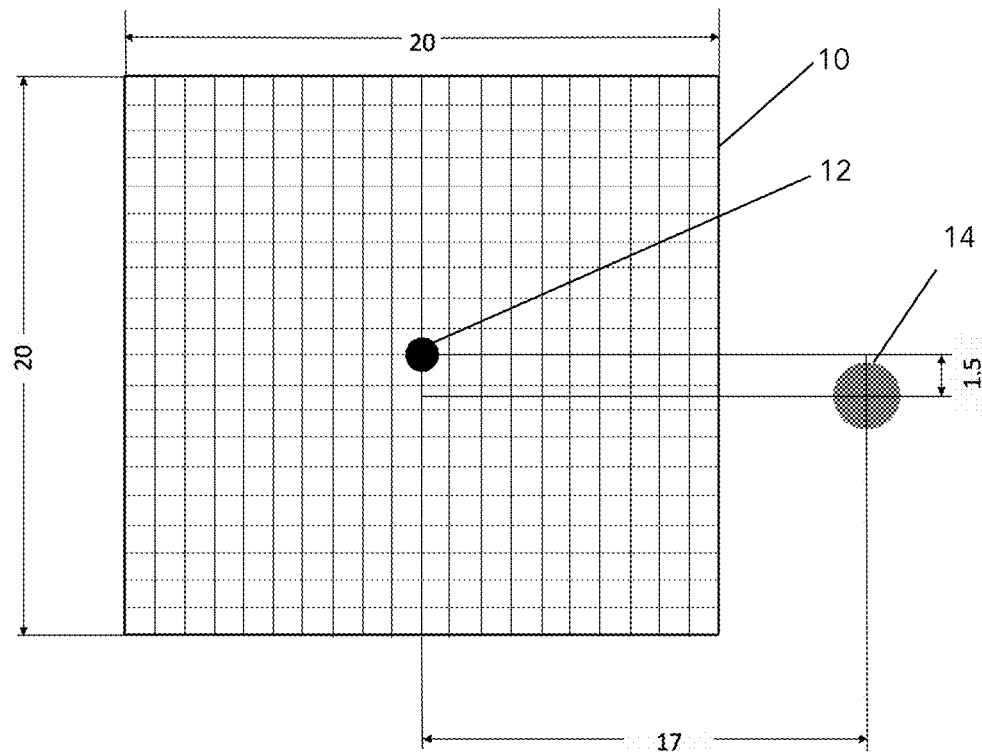
FIG. 6A illustrates a right eye test with a visual grid.
Figure 6B:
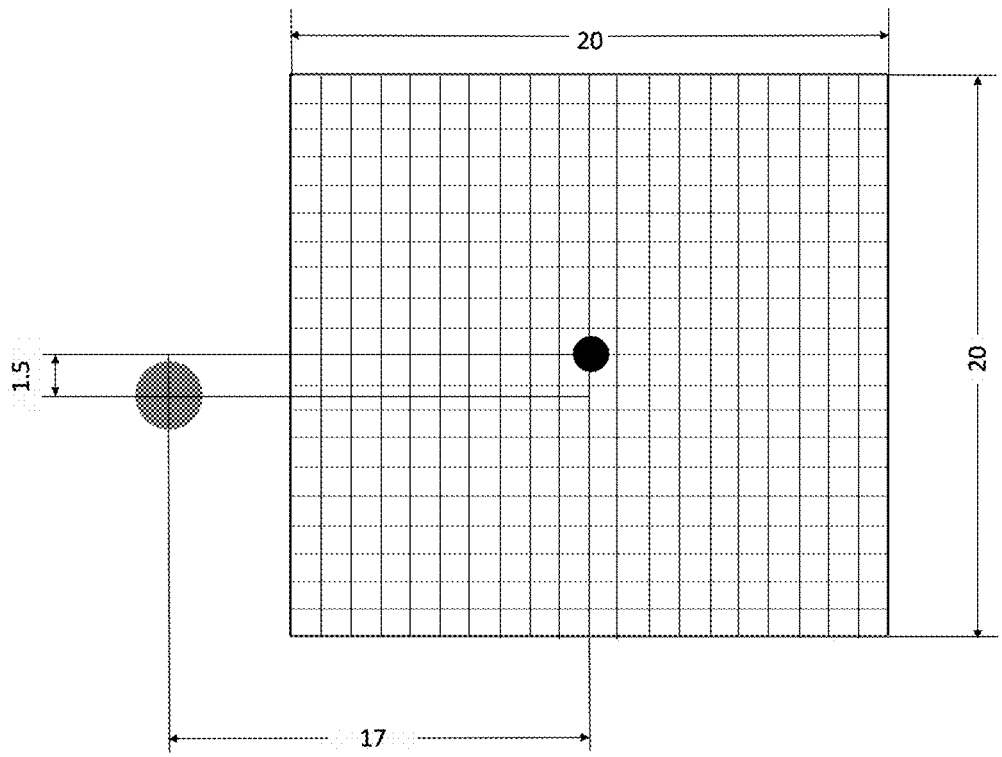
FIG. 6B illustrates a left eye test with a visual grid.

The peripheral reference 14 is a reference outside the visual grid and can be, for example, a circular disk with a diameter of the order of 10% to 15% of the matrix dimension placed outside the matrix along the center horizontal line, to the right of the matrix for testing the right eye, and left of the matrix for testing the left eye. The peripheral reference, also referred to herein as the reference measure, is preferably placed slightly below the center horizontal line with the disk center away from the horizontal line approximately 7.5% of matrix dimension below and a distance of approximately 85% of the matrix dimension away from the center to the right (or left) as shown in FIGS. 6A and 6B. This peripheral reference 14 or reference measure disk will be on the left side of the test grid when testing left eye and right side for the right eye testing.

Figure 3B:
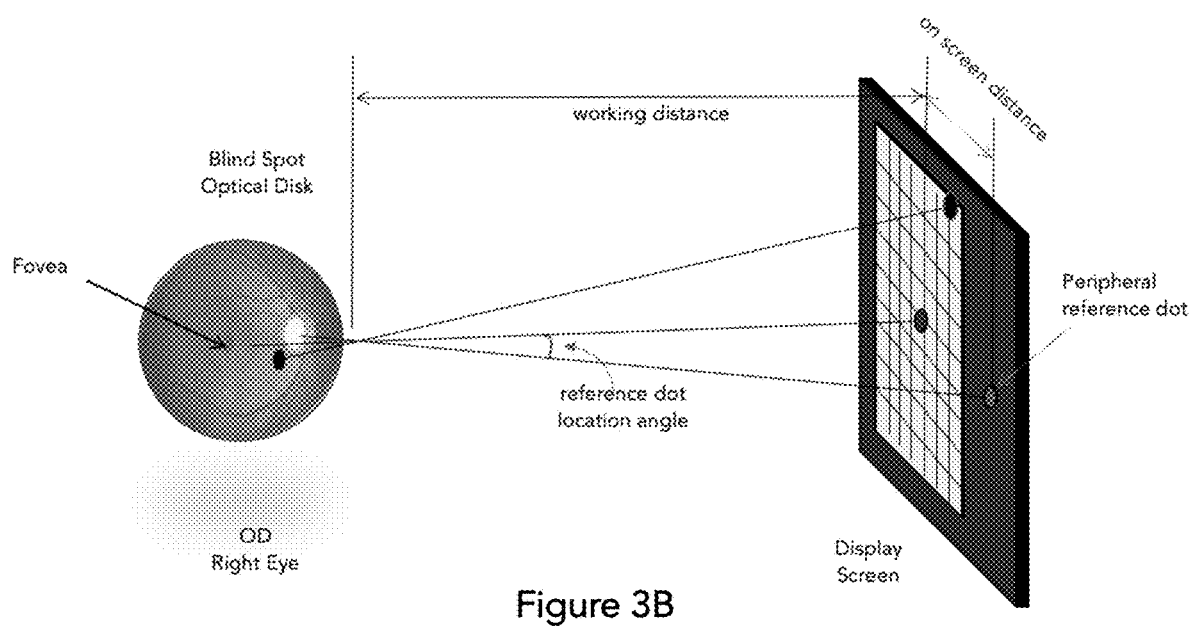
FIG. 3B shows the triangular relationship between working distance and location of the reference dot in an Amsler test.

FIG. 3B depicts what an eye observes when undergoing an Amsler grid test. The triangular relationship between the working distance and location of the peripheral reference dot is shown. Depending on the working distance the matrix represents different retinal test coverage area or equivalent viewing angle, with a recommended working distance is such that the matrix covers approximately +/−10-degrees of central vision in the horizontal orientation, and each square box in the square grid representing 1 degree by 1 degree in the retina. The visual grid preferably covers a field of view of +/−10 degrees of the field of vision in all four directions when the said device is placed at a proper working distance away from the patient's eyes.

To set the proper working distance, the user places their head at a distance from the screen approximately equal to three times the distance between the reference measure disk and the center spot of the matrix on the display screen. The user then moves their head towards or away from the screen until noticing that the reference measure disk disappears, thereby establishing the proper working distance. The patient maintains this distance to perform the central vision test. When performing tests at this proper working distance, the test pattern matrix covers exactly +/−10 degrees in both horizontal and vertical directions; hence, each grid represents 1 degree in the retina. As long as this method is followed to establish the working distance, the test accuracy will be maintained independent of the display screen sizes. However, as the screen becomes larger the working distance increases proportionally, once it is longer than a full arm's length for a person, it would not be practical to do any markings, so in reality there is a practical limit to the screen size. Another limiting factor to the accuracy is due to the fact that the exact location of the blind spot varies from individual to individual, using a fixed reference measure spot in the test pattern may not reach the desired test accuracy. This can be addressed using the programmable location method described below. The high test accuracy allows marked results to be translated onto the person's retinal map more correctly.

Preferably, the horizontal location of the blind spot is calibrated for each eye and each user during setup. The method for blind spot calibration involves using a calibration pattern similar to the said test and placing the display device at a predetermined distance from the user's eye based on the display screen size. With a test pattern placed at the proper distance, a patient can actually experience the said blind spot. Taking advantage of this biological and visual feature of the eye, a proper working distance can be found and established. Since the exact location of the blind spot varies from individual to individual, a fixed test pattern will not reach the desired test accuracy. For blind spot calibration one eye is calibrated at a time. The untested eye is covered and the patient gazes at the center reference dot, also referred to herein as the central reference. The calibration is then started, and the program will move the reference measure spot on the display device from the location close to the matrix slowly moving outwards. At a point where the peripheral reference spot just vanishes or disappears from the view completely, the user signals to the device/application through a designated button or input that the peripheral reference has disappeared, indicating that the peripheral reference is positioned at the blind spot. The location of the spot is registered. This test is then repeated, preferably at least three times, and the location of the inner edge of the blind spot with respect to fixation is registered and used for all future testing regardless of the display platform type or model. This is then repeated for the other eye. The calibration data defines the actual location of the blind spot in angular value. This calibration value can then be used to improve the accuracy of the central vision test by performing the said test with the location of the reference measure spot set according to the calibrated value. By adopting this method, the scale of the test pattern matrix is adjusted to be +/−10 degrees if a patient user performs the test at the working distance. Alternatively, the patient performs the test with the test pattern described above at a distance comfortable to the patient; the calibration on the actual blind spot location angle will then be used to scale the patient test data which can be projected onto the retinal map accordingly.

Figure 4:
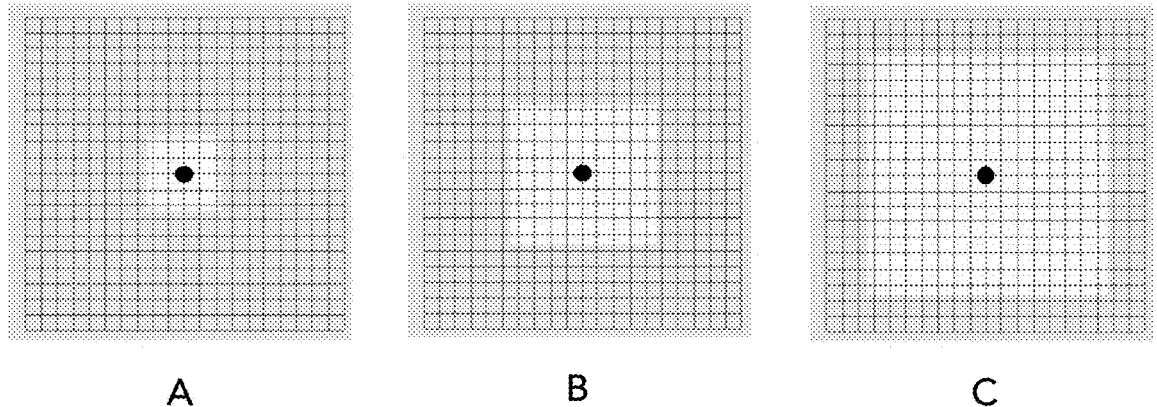
FIG. 4 shows an Amsler grid with three different shaded backgrounds.

FIG. 4 shows snapshots of an Amsler grid with three different shaded backgrounds for the test pattern during a cycle of progressively changing background shades. In the present disclosure the background behind the visual grid or matrix is programmed at the electronic device to dynamically change in level of color, contrast, brightness, shade, texture, contour, or a combination thereof. Changing the level of background shading, for example, creates a mild but constantly changing background, helping to eliminate the filling-in effect. The time-based progressive contrast change creates a perceived motion in the backdrop of the field, thus countering visual filling-in, via the principle of destabilizing edge adaptation. Examples of background patterns include a concentric shade change, vertical shade change, horizontal shade change, or diagonally. Texture changes can include, for example, patterns of squares of different contrast, a contour or a ring slowly changing or moving, or other texture changes. One example of sequential screenshots of the time-based progressive feature along with the visual grid space is shown in FIG. 4. It is understood that this set of varying background images is merely representational and that the implementation can include a multitude of sub-steps between different changes in the background pattern.

The timing of the background change during the test hinders the filling-in effect by disabling the patient's inclination to fill in a visual area as there is no consistent background by which to fill. Weerd et al. (Perceptual filling in: a parametric study. *Vision Research* 38 (1998) 2721-2734) found that on centrally fixated viewing of a stable visual field, for a target or a scotoma of 1 degree spread or diameter, at eccentricities falling in the outer edges of the macula, in the peri-foveal region, that is 8 to 12 degrees eccentric to the central fixation, filling-in happens in 4 seconds. It has also been found that the time to fill-in increases as the eccentricity of the location decreases with respect to the central gaze. If the field is destabilized with either the change in brightness, texture or color periodically but progressively covering the entire field within a time interval of less than 4 seconds, filling-in may be considered to be addressed. Furthermore, according to Ramachandran and Gregory, (Perceptual filling-in of artificially induced scotomas in human vision. *Nature* Vol. 350, 25 Apr. 1991) if at all a partial filling-in happens in any region of an existing scotoma, there is no carried over effect, or at subsequent times the filling-in happens from the edges of the scotoma, although the time to completely perceptually fill-in is reduced. Progressive visual perception of motion can enable addressing of the perceptual filling in effect. As provided by Welchman and Harris (Filling in the details on perceptual fading. *Vision Research* 40, (2001), 2107-2117), adaptation beyond just the dynamic change of the luminance, texture is needed to pave the way for filling in. Rapid cyclic destabilization such as, for example, a time based concentric translational progressive or declining feature related to contrast/shape/texture in the background covering the entire visual field counters the edge adaptation of the contour of the scotoma, thus addressing the perceived filling in.

Troxler fading is another critical jeopardizing factor that occurs with continuous central fixation and viewing of a stable field, such as that associated with standard Amsler grid testing, that can be addressed by the present system. May et al. (Disappearance elicited by contrast decrements. *Perception & Psychophysics* 2003, 65 (5), 763-769) posit that such fading happens from the periphery of the visual field and progressively approaches the centre. Troxler fading at the visual periphery may lead to erroneous interpretations of the features of the visual field. The rate of Troxler fading can be slowed with an enhanced contrast between the backdrop and the regions of interest, with such a contrast arrangement may also be believed to delay the filling-in effect (Motion-Induced Blindness and Troxler Fading: Common and Different Mechanisms. *PLoS ONE* 9(3), 2014) and the onset of Troxler fading and perceptual filling-in are unavoidable artefacts of fixated viewing of a stable field of supra-threshold level (Contrast dependency in perceptual filling-in. *Vision Research* Volume 46, Issue 20, October 2006, Pages 3304-331). McCamy et al. (Microsaccadic Efficacy and Contribution to Foveal and Peripheral Vision. *The Journal of Neuroscience*, Jul. 4, 2012, 32(27):9194-9204) reported that independent of the contrast, a target presented 9 degrees eccentric to the central fixation in a stable visual field, undergoes Troxler fading every 7.5 seconds and the intermittence of fading increases as eccentricities are reduced.

To simultaneously counter the perceptual filling-in and the Troxler fading, if the total area encompassed by the background field is destabilized cyclically by implementing a concentric progressive translational change in brightness with a periodicity of less than or equal to about 4 seconds for the entire area of the scene encompassed by the field, then there is the possibility of simultaneously addressing filling-in and Troxler fading phenomena. For a monochromatic field, the grayscale is the measure of luminance with luminance being the closest objective parameter that can be considered to relate to brightness. Introducing grayscale or brightness variation is a very effective way of generating dynamic background. In the digital and/or electronic implementation, adjusting the greyscale and/or brightness of the image and/or background would allow setting the appropriate levels of variation in shade in such a way that they are sufficient to break up the filling in effect at the same time without creating any disturbance to central gazing during the test.

The standard Amsler grid test can be conducted at suprathreshold contrast level between the background and the grids. However, it is established that testing under threshold contrast settings between the background and the grids is more effective, especially for early detection of scotomas and for detection of relative scotomas (M. Wall and A. Sadun, "Threshold Amsler grid testing. Cross-polarizing lenses enhance yield", Arch Ophthalmol 1986 April; 104 (4):520-3). Threshold Amsler grid testing increases both the number of defects found and the total area of these defects compared with the standard suprathreshold Amsler grid. Threshold Amsler grid has been effectively used for diabetic retinopathy monitoring, in addition to age related macular degeneration monitoring. It has also been used as a screening tool for a variety of clinical studies including asymptomatic patients on hydroxychloroquine therapy (A. Almony et al., "Threshold Amsler grid as a screening tool for asymptomatic patients on hydroxychloroquine therapy", Br J Ophthalmol 2005; 89:569-574.) In Threshold Amsler grid testing the existing threshold Amsler grid is established by decreasing the illumination of a white Amsler grid to the level at which the grid can just be seen, hence the threshold. The patient would then adjust the illumination barely above the threshold and perform the usual Amsler grid tests. In the embodiment described on a display screen, initially the grids may be set at the same "0" or least level brightness (luminance) and then adjusted incrementally until they become barely visible with respect to the background.

In an embodiment of the present invention, the threshold grid method is implemented in reverse contrast to the reference, that is with the dark grid pattern generated on the display of an electronic and with the background illumination level fully adjustable. Since the grid lines are dark lines, as the background brightness increases the contrast between the background and the dark grid lines then increases. A pre-test for threshold detection of the visual grid relative to the background can be conducted by gradually increasing the brightness level of the background starting from a dark screen to the threshold of visibility to establish a threshold baseline first. This threshold level is different for different scotoma or person. After the threshold level is established, the patient would increase the illumination or grey level slightly above the threshold and perform the tests. It is understood that the opposite can also be used, i.e. a light coloured grid on a dark background, and the grid lines can be lightened relative to the background.

To enable a greater light in-flux it is preferable that the test is not executed under bright ambient settings which reduces the pupil size, and in turn reduces the light influx. This makes the task of detection unnecessarily difficult for the patient. Since the absolute contrast sensitivity measurements are not the purpose of the testing, pertinent result can be achieved with the brightness level of the display device being adjusted to the patient's comfort level with proper but darker ambient brightness so that patients pupil size are not significantly reduced. Although this form of Amsler testing has its benefit as cited earlier, the reduction in contrast may have elevated filling-in effect to set in earlier than at the non-threshold grid tests (Y. Sakaguchi, "Contrast dependency in perceptual filling-in". Vision Research Volume 46, Issue 20, October 2006, Pages 3304-3312). The dynamic background change, i.e. a progressive contour either expanding or contracting around the brightness level as described above may be applied. With the threshold method the dynamic background change would be around the brightness level established above.

Figure 5:
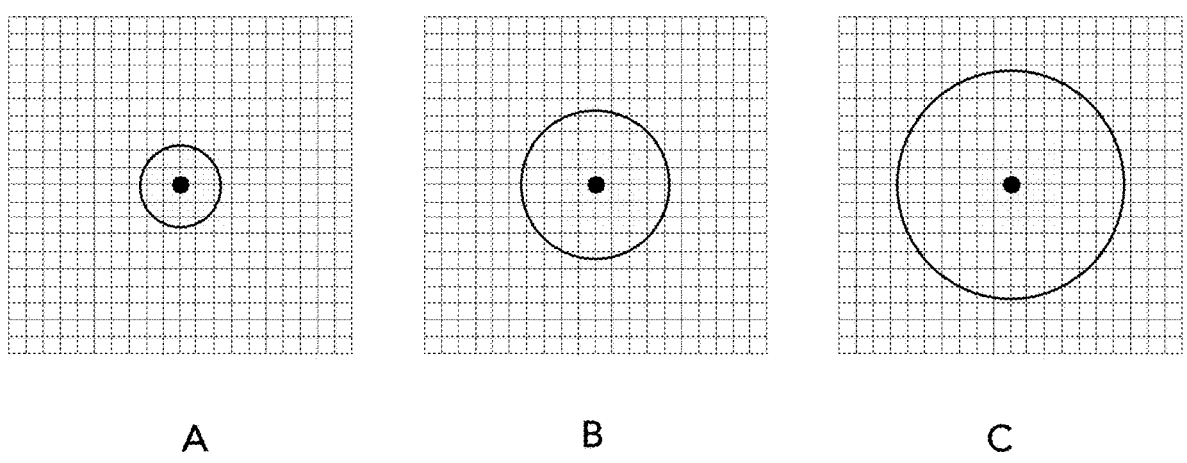
FIG. 5 shows an Amsler grid with three different contour backgrounds.

FIG. 5 shows an Amsler grid with three different contour backgrounds. Varying a contour while maintaining the visual grid stationary also enables breaking up of the filling-in effect and/or Troxler fading.

FIG. 6A illustrates a right eye test with a visual grid and FIG. 6B illustrates a left eye test with a visual grid. The central black dot is the gazing point or central reference 12 on the visual grid 10 for the visual test and the grey dot provides a peripheral reference 14. These visual reference points assist in calibration of the visual grid of a patient's eye. A peripheral reference 14 is preferably located along and slightly below the center horizontal line and outside the said matrix to position the electronic display device at a good working distance for the testing. As shown the center of the peripheral reference 14 is at a distance of 17 gridlines from the center of the test grid, equivalent to 17 degrees from the centerline of the visual field, however the location can be, for example, between 14 and 20 degrees based on device and patient calibration and distance of the device from the patient. By utilizing the individual human eye's natural blind spot the proper working distance for performing the said tests can be established. FIG. 3B shows the relationship between the blind spot (optical disk) and the peripheral reference.

When patients use the device to test the vision of their right eye as shown in FIG. 6A, the peripheral reference 14 is positioned on the right side of the matrix. Likewise, when testing the left eye as shown in FIG. 6B, the peripheral reference 14 is positioned on the left side of the visual grid 10. The placement of the peripheral reference 14 is variable with a nominal center position at a distance approximately 1½ (vertical)×17 (horizontal) of grid line from the center of the visual grid such that the distance between the central reference 12 and the peripheral reference 14 corresponds to that between the fovea and the optical disk when the testing device is placed away from patient eyes at a specific distance. This distance is referred to as proper working distance.

Since the optic disk is a natural blind spot of human eyes and the center of the blind spot is between 14 to 20 degrees away from the fovea, an individually based blind spot calibration can be introduced. To calibrate the test using a peripheral reference disappearance method, the triangular relationship of working distance to the peripheral reference can be used as shown in FIG. 3 by placing the electronic display device at a predetermined fixed working distance, then allowing the peripheral reference 14 to move from the location closest to the border of visual grid to further away (farther right for right eye, or farther left for left eye) until the peripheral reference 14 disappears into the patient's blind spot. At this point the peripheral reference 14 can be fixed and the distance recorded based on the position on the visual grid test pattern. This is the calibrated location for the particular patient and the particular eye. In addition, performing the test using the peripheral reference disappearance method is an assurance of observing the correct working distance during testing. A pre-set location can also be used for future testing.

The electronic device for displaying the visual grid 10 typically includes a display screen and a variety of computer readable media. Such media can be any available media that is accessible by the electronic device and includes both volatile and non-volatile media, removable and non-removable media. The system memory includes computer readable media in the form of volatile memory, such as random access memory (RAM), and/or non-volatile memory, such as read only memory (ROM). The system memory typically contains data and/or program modules such as operating system and application software that are immediately accessible to and/or are presently operated on by the processing unit. The electronic device may also include other removable/non-removable, volatile/non-volatile computer storage media which can provide non-volatile storage of computer code, computer readable instructions, data structures, program modules, and other data for the electronic device. Each of the operating system and application software (or combination thereof) may include elements of the programming and the application software to generate the test pattern and record the test results; which can also be stored on the mass storage device in any of one or more databases or cloud computing and storage facilities known in the art. The system can also preferably be connected to the internet to provide the testing results to a medical professional or system for analysis, or stored or analysed remotely on a cloud-based server.

One alternative to Amsler testing for self-monitoring standards of central retinal vision while still employing subjective test protocols is to utilize the principle of preferential hyperacuity perimetry (PHP), threshold of shape distortion or Snellen and contrast sensitivity testing. PHP, also known as vernier acuity, which utilizes the ability of the subject to identify misalignment in objects making up the visual field. The capacity to identify edges of the objects present in the visual field is a highly sensitive metric. In a degenerative retinal condition therefore changes in vernier acuity responses can be observed far earlier in the stage than other responses which are known to show decline at advanced stages of the diseases, with one such popular testing being that of visual acuity. To test for PHP, the area of the macula is scanned with a succession of stimuli, the stimulus being composed of a series of dots either arranged horizontal or in vertical direction. In each such line consisting of interspaced dots there are dots which are intentionally misaligned, thus resembling a bump or a partial wave. The patient's task is to visually perceive and report the location of the distortions while keeping their gaze fixed centrally. If the retina under consideration is undergoing degenerative changes, the distortion is likely to be reported in the region other than the pre-set location of the artificial distortion, at the site of the ongoing degenerative changes. The patient is subsequently required to mark and/or report the location of the perceived distant distortion from the pre-set distortion. The distant distortion reported is considered as the pathological distortion. By suitably analysing the amplitude of the pre-set or artificial distortion, the area of the pathological morphology with the existing retinopathy can be computed or quantified. Normalization of test results is executed to test if the results are within the expected normal limits.

The PHP testing, although addressing the psychophysical shortcoming of perceptual filling in and the Troxler fading and potentially enable point the area of anomaly, is unable to report the morphosis of the patient's visual acuity changes, that is whether a scotoma is resulting in the area or not, from the progressive neovascularization, or the exact type of anomaly observed in the field of view. Also, with dots being in motion it is likely the patient may have the inadvertent urge to follow a motion, thus losing fixation. Such a challenge has been cited as jeopardizing the use of external fixation while reporting a peripheral flicker null position while performing flicker photometric testing for quantifying the levels of macular pigment in the eye. Furthermore, the test generally requires line by line scanning to cover a considerable area of the macula, making the PHP test long compared to the visual field-based testing as such on an Amsler grid whereby the entire macula is sampled together.

Figure 7A:
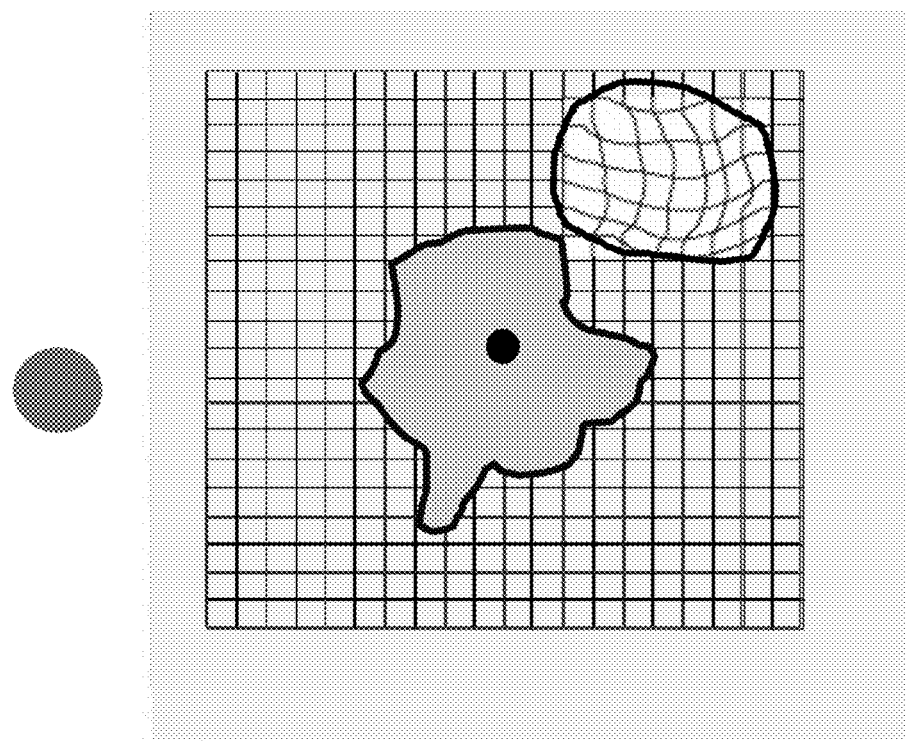
FIG. 7A is a left eye test result of a patient with visual distortion.

FIG. 7A is a left eye test result of a patient with visual distortion, recorded and redisplayed. In this hypothetical example, two abnormalities are shown: one for wavy lines and the other missing lines. Alongside the psychophysical and neuro visual challenges, in order to optimize the fixation and sampling the correct area of the field pertinent to the retina, the optic disk or biological blind spot (scotoma) in the human eye has been utilized to assist distance control for consistency in tests. The center of the blind spot is located about 14-20° from fixation and 1.5° below the horizontal meridian and is roughly 7.5° high and 5.5° wide at complementary locations in each eye. The reason that in daily life one does not observe such a region of void under general viewing conditions is due to the complementary positioning of the optic disk during binocular vision and perceptual filling in during monocular vision as mentioned above, whereby the information from the surroundings in the immediate vicinity of the optic disk is continued into the region of the scotoma.

Patients with pathological changes progressing towards maculopathy report distortion of edges or boundaries of objects in their visual field demonstrating aberrations of the retinal morphology associated with maculopathy. Shape discrimination hyperacuity (SDH) testing generally involves a visual task which requires participation of other areas of the retina beyond the area of the spot where an external stimulus is mapped. Such a global involvement makes it difficult for individuals with the onset of AMD to identify distortion of shapes and hence progressively report a change in threshold with the deteriorating conditions in the retina, especially the macula. Individuals being tested on the SDH protocol often report that the threshold at which circular contours in the form of radial frequency patterns appear distorted with respect to a perfect circular shape. The SDH testing, although it can be readily implemented on a modern-day touch enabled smartphone, suffers from the severe limitation that it can only sample the portion of the stimulus which map within the reaches of the fovea. An alternative which possibly addresses the spatial limitation of the SDH is the contour integration (CI) test protocol. Although the test requires central gaze fixation, it requires post presentation response of the location of the modulated arc, which is of limited stretch and width. Thus, CI testing requires significant number of trials for testing a particular eccentric outreach in the retina, making it suitable for testing standard locations of the retina such as the boundaries of the Early-Treatment Diabetic Retinopathy Study (ETDRS) grid but not sampling the entire area covered by the macula. Similarly, the visual acuity (VA) and contrast sensitivity (CS) testing has the limitation that the tests by themselves may show an age-related decline even for a healthy retina.

Figure 7B:
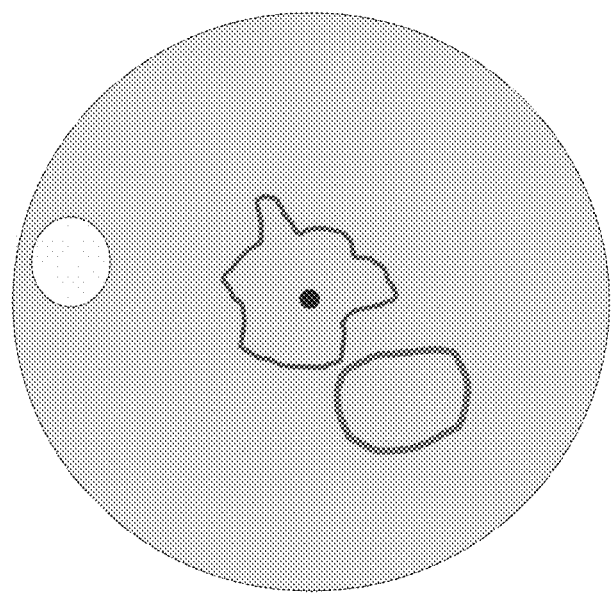
FIG. 7B is the result from FIG. 6A projected on a retinal map.

FIG. 7B is the test result from FIG. 7A projected on a retinal map. The principle of the projection is based on the mirror relationship between an image and/or pattern a person sees and where it is projected on the person's retina as indicated in FIG. 3B due to the lens function of the human eye. For example, an area of missing lines on the upper right corner of the test grid seen by a patient's right eye is an indication of a scotoma on the lower left of the retina of the patient's right eye from patient's own prospective. Furthermore, when another person such as an eye care professional is looking into this patient's right eye, i.e. through an ophthalmoscope or fundus imager, they may see an atrophy and/or edema causing the scotoma on the lower right corner. This is due to the fact that the eye care professional as an observer has turned around 180 degrees from the prospective of view of the test grid compared to the patient to look into the patient's retina. The location accuracy of the reported abnormalities depends on the proper working distance procedure being followed during the test as recommended above with reference measure spots calibrated according to the location of the optical disk in an individual's eye as described above.

The projection of the test result onto the patient's fundus image or retinal map has two main steps. The first step is to convert the object view test result as seen on the screen into a retina view image. In this exercise, the object view image is first mirrored vertically by flipping upside down around a horizontal axis right on the center grid line and then scaled with location defined on the +/−10 degree Amsler grid. The natural optical disc symbol should be added to this map on its proper location. The retina view image reporting the test results is thus created. The second step is to project the retina view image of the test results to the patient's fundus image. This step utilizes a common image processing method known as registration to adjust (scale, rotate, and stretch) one image to seamlessly map on to the other.

Figure 8A:
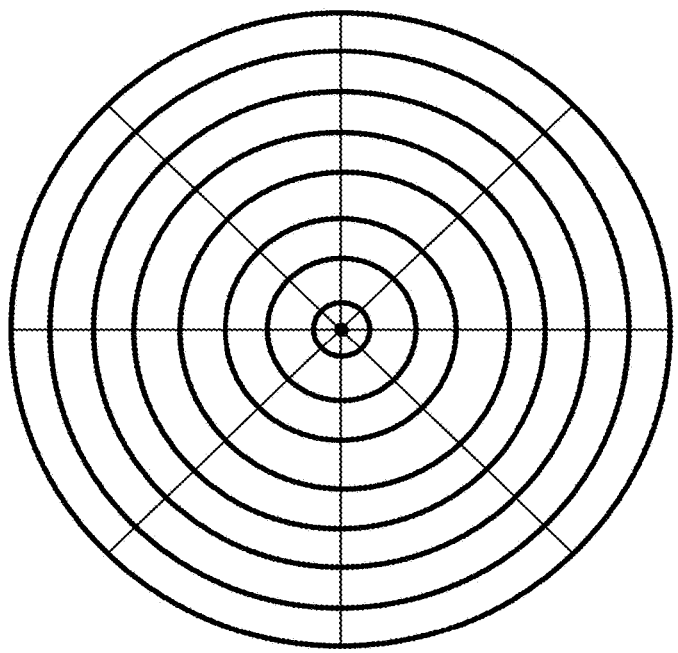
FIG. 8A is an alternative bullseye style grid.
Figure 8B:
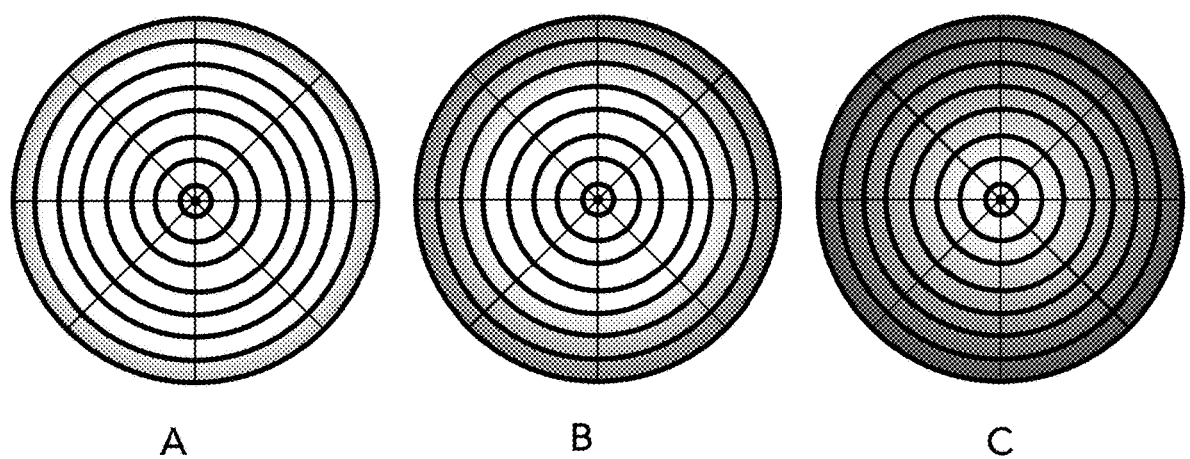
FIG. 8B is a bullseye style grid with variable background shading.

FIG. 8A illustrates an alternative bullseye style grid with a radial grid emanating from a central reference. This bullseye style grid may be an alternative to the traditional square boxes or matrix-based Amsler grid. FIG. 8B is a bullseye style grid with variable background shading in accordance with the present invention.

Figure 9:
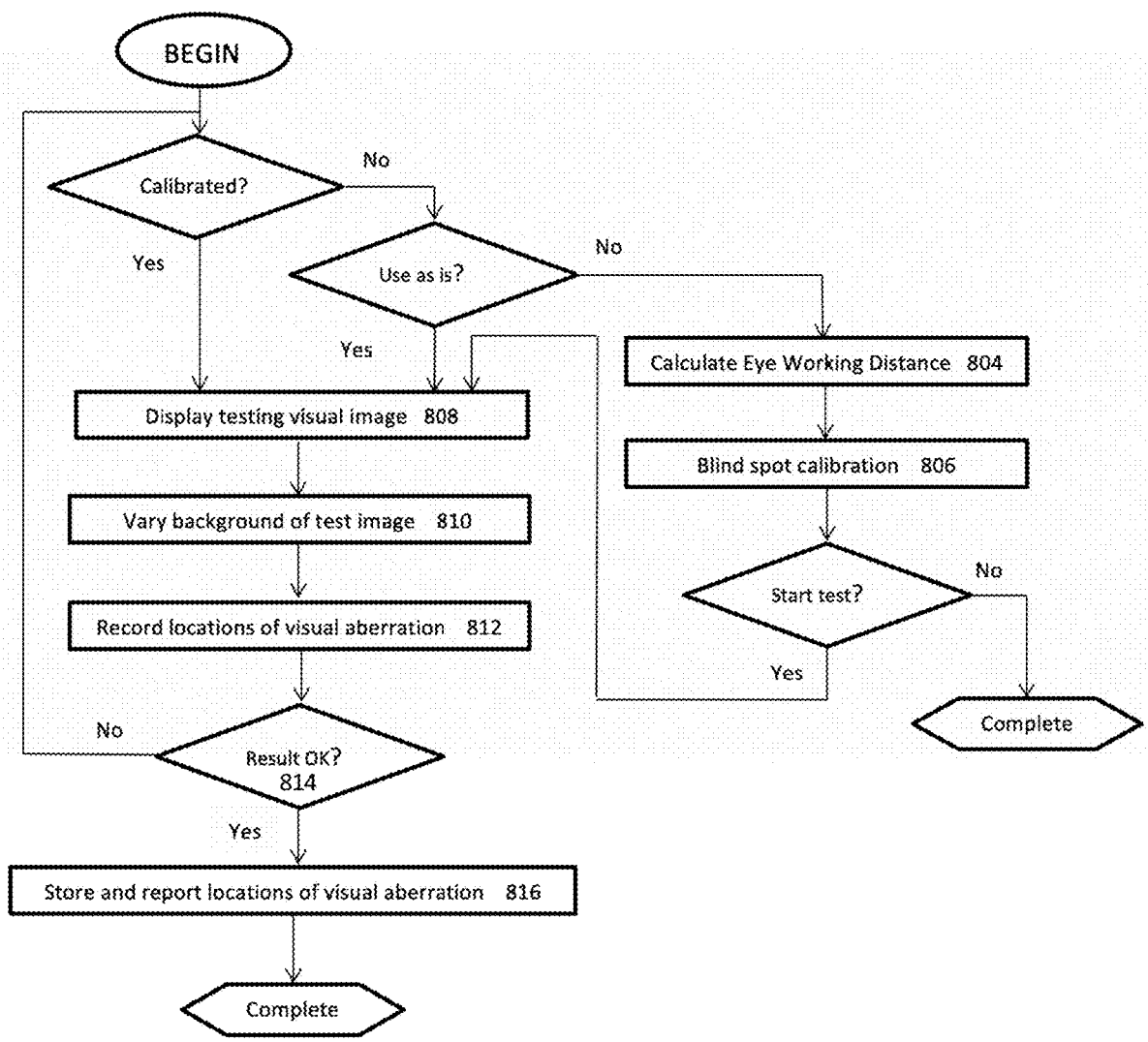
FIG. 9 illustrates a method of generating a visual image for central vision testing.

FIG. 9 illustrates a method of generating a visual image for central vision testing on an electronic display device. The method is divided into two parts: in the first part a patient's eye optic disc location is calibrated, and in the second part the monitoring test is done. The purpose of the first part of the test, i.e. the location calibration, is to set the peripheral reference dot in the correct location relative and according to the actual location of the optic disc for each of the patient user's eyes. The principle of the calibration is described above in the description of FIGS. 3A and 3B. In the calibration process the system: (1) calculates the working distance for the given display screen size used 804; (2) sets the distance between patient's forehead and display screen equal to the working distance; (3) moves the peripheral reference dot away from the grid until it disappears into the patient's blind spot; (4) stops the peripheral reference dot from moving; and (5) stores this location for the person and for the particular eye. This results in a blind spot calibration 806 for one eye of the patient. The same calibration completed for first eye is then repeated for the second eye. In the second part is the actual performing of the visual acuity test.

The test starts with the login to make sure the correct calibration data exists and is used for the patient's tests. If the patient's calibration data does not exist, then the system with either perform a calibration or skip the calibration and accept the warning about inaccuracy and proceed with the test. Following that is preparation for performing the test, which is the same as setting the right working distance for calibration. The working distance can either be preset according to the calculation from the display screen size or moving head away from close to the display screen position till the peripheral reference dot disappears, at this point the working distance is reached. With the working distance set, starts the test. The display then presents a visual image to the patient 808 and the background will be varied of the test image 810 including change of the shade progressively and cyclically according to the pre-set pattern dynamics/programs. Patients will mark or record any visual abnormalities or visual aberration 812 during the test. The marked data indicating location, shape and area of the missing or distorted lines can be redisplayed to the patient for confirmation of the sites of visual aberration. Optionally, the test can be compared to previous test from the same eye of the patient to consider whether the obtained results are consistent with previous results 814. Artificial intelligence may be used in conducting the comparison and progression assessment. If the results are determined not to be consistent with previous results the test can be run again, optionally with recalibration. The locations of visual aberration can then be reported and stored 816. Reporting recorded vision abnormalities or visual aberrations can include, for example, uploading data to an archive or database, providing and/or displaying the results to the patient, grant permission for access data by a healthcare provider or family member. Artificial intelligence on patterns of symptomatic retinal features can also be used based on reports by patients on testing to further understand disease progression to provide data for tracking and early detection as well as correlation between disease progression and other parameters such as treatment, procedures, supplement usage, lifestyle etc.

Once verified, the data can be uploaded and stored in the device or more likely in the cloud and/or internet storage. In one example, the test pattern and visual testing image can be stored and run from a piece of application software loaded on the display device memory, where the device can be, for example, a tablet device, a computer, a smart phone, or any computing device with or connected to a visual display. In such a case, the application software can generate the test pattern and visual grid at an appropriate size and automatically scaled to any given aspect ratio of the display screen. More generic applications may, for example, involve the generation of the test pattern and visual testing image in a cloud hosted server that is easily accessible by users through any common web browser on a computing device with display monitor or mobile devices such as a tablet or a smartphone. The preferable usable display diagonal size is between 7 inches and 14 inches. To minimize the errors and maximize the test accuracy, the most preferable size for a display screen is between about 9-11 inches diagonal.

Figure 10:
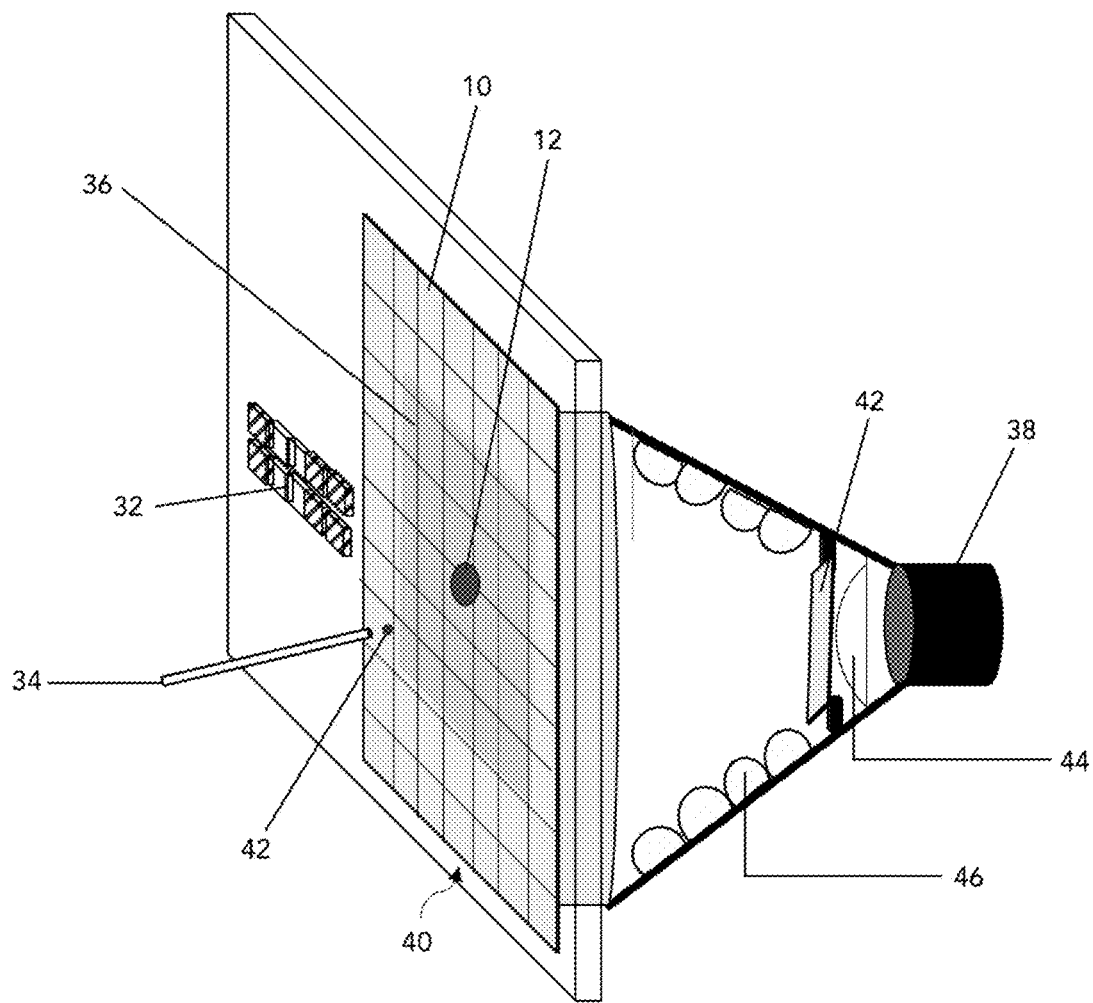
FIG. 10 illustrates an isometric view of a standalone electro-optic system.
Figure 11:
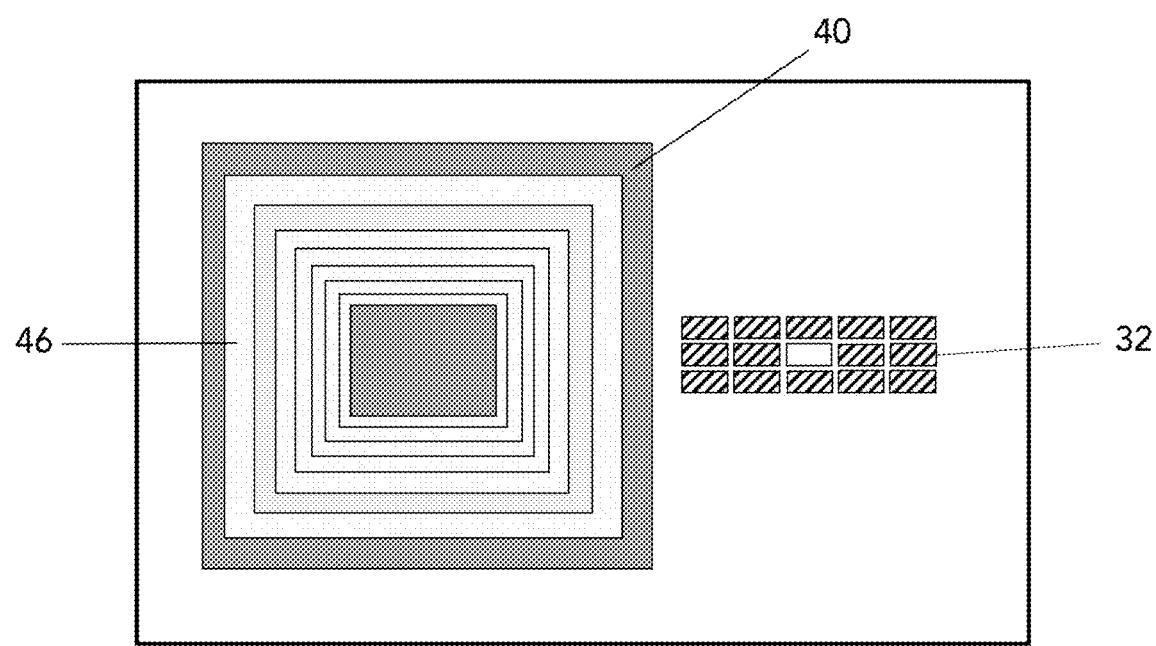
FIG. 11 illustrates the rear view of an electro-optic system test panel.

FIG. 10 illustrates an isometric view of a standalone electro-optic system. The vision testing apparatus setup can be provided as a standalone electro-optic system that does not require a touch-based LCD screen, but as a simple dedicated, electro-optic, stand-alone device. The shown device has a viewing plate with fixed test pattern as a visual grid 10, controllable backlighting 36, a marking device 34 such as a stylus, laser pen, light pen, and a sensor device 38, shown as a camera, for the marking of the user. The device can also have a spectral filter 42, a camera aperture and lens 44, and LEDs or other lighting device behind the screen for back lighting 46. Other sensor device can be used, including a touch-sensitive screen. A visual grid 10 can be imprinted on a semi-transparent or translucent diffusing plate which serves as a viewing screen 40. The central reference 12 as a fixation spot is printed in the center of the grid. LEDs positioned on the side of the grid as shown in FIGS. 10 and 11 serve as peripheral references to set the proper working distance for left (FIG. 10) eye tests and right eye tests by rotating the device upside down. Instead of LEDs, a dark spot can be printed on the position-to serve as the peripheral references to set the correct working distance. Alternatively, peripheral reference can be replaced as shown by a peripheral reference array 32, which is an array of LEDs. In this configuration only one of the LEDs in the array will be lit according to the calibration at the working distance to represent the blind spot of the individual particular. The LED-array for blind spot detection can also optionally be programmable. Behind the viewing screen is controllable backlighting 36 for controlling the background brightness. The controllable backlighting 36 can be, for example, an array of miniaturized LEDs providing backlighting for the viewing screen. The controllable backlighting LED arrays can also optionally be programmed to adopt the ambient lighting conditions, and the device can further comprise an ambient light sensor. More significantly, the controllable backlighting 36 can be programmed in such a way that it can periodically change illumination brightness levels in a pattern progressively and concentrically outwards. This repetitive cyclic alteration of the background illumination level discourages the filling-in and the Troxler fading during the vision testing. The input device 34 can be a light pen made of a small LED attached to a stylus or simply a laser pointer that will be used with a close proximity to the test surface for the patients to mark the area of interest 42 or deterioration. The sensor device or camera can also take one or more consecutive images or videos to record the movement of the marking device.

FIG. 11 illustrates the rear view of an electro-optic system test panel. Behind the viewing screen 40 is a digital camera with a filter to block off ambient and illumination light and only allows light from the light pen. In this way, the filter can attenuate light and blocking out undesired spectra of light. Backlighting 46, which is optionally a backlighting LED array, provides dynamically changing brightness to the viewing screen. A peripheral reference array 32, which is preferably a programable LED assembly, can be provided as a blind spot detection feature for calibration. The collection of consecutive images or videos indicate the patient marked area, and provide the record of the tests. The device can also be connected to a computer and the test data processed and stored locally. The sensor device or digital camera can additionally or alternatively be web based and connected on-line, directly or through a computer to allow test data to be processed and stored in a private and secured cloud and/or transmitted to a medical professional or site for analysis.

All publications, patents and patent applications mentioned in this specification are indicative of the level of skill of those skilled in the art to which this invention pertains and are herein incorporated by reference. The invention being thus described, it will be obvious that the same may be varied in many ways. Such variations are not to be regarded as a departure from the scope of the invention, and all such modifications as would be obvious to one skilled in the art are intended to be included within the scope of the following claims.

The invention claimed is:

1. A method for vision testing comprising:
   displaying, on an electronic display device, a testing image comprising a static visual grid, at least one visual reference point, and a dynamic background;
   positioning a person at a working distance from the electronic display device;
   dynamically changing the dynamic background cyclically and concentrically with the visual grid to change at least one of the background color, brightness, shade, and texture at a frequency sufficient to interrupt at least one of the Troxler effect and the filling-in effect; and
   receiving input for recording location of any perceived visual aberration relative to the visual grid.

2. The method of claim 1, wherein the grid is a square grid, rectangular grid, or bull's eye grid.

3. The method of claim 1, wherein the at least one visual reference point is a central reference in the visual grid.

4. The method of claim 1, wherein the at least one visual reference point is a plurality of dots equidistant from the centre of the grid.

5. The method of claim 1, wherein the electronic display is a touch display, and receiving input for recording is done by touching a location on the visual grid at one or more location of any perceived visual aberrations in the visual grid.

6. The method of claim 1, wherein the visual grid covers a field of view of +/−10 degrees at working distance during the testing.

7. The method of claim 1, wherein at the working distance a peripheral reference dot disappears into the blind spot of the person's eye undergoing testing.

8. The method of claim 1, further comprising creating a retina map comprising the location of any perceived visual aberration where the visual aberration is recorded.

9. The method of claim 1, wherein the electronic display device is a computer monitor or a tablet screen.

10. The method of claim 1, wherein the dynamic background change has periodicity of less than or equal to 4 seconds.

11. The method of claim 1, further comprising using a peripheral reference array to calibrate the working distance.

12. The method of claim 1, wherein the method is used in detecting one or more retinal disease.

13. The method of claim 12, wherein the retinal disease is macular degeneration, diabetic retinopathy, or glaucoma.

14. The method of claim 1, wherein the input for recording is from a mouse, stylus, or finger.

15. The method of claim 1, wherein the background brightness of the testing image is adjustable and can be reduced to a threshold level with respect to the grid to conduct threshold central vision testing.

16. A vision testing apparatus comprising:
   a viewing device comprising a visual grid on a transparent viewing screen;
   a programmable backlighting device behind the viewing screen for backlighting the visual grid to create a dynamically changing background sufficient to interrupt at least one of the Troxler effect and the filling-in effect; and
   a camera device behind the backlighting device to capture a location of visual aberration as indicated by a user.

17. The apparatus of claim 16, wherein the programmable backlighting device is an LED array is programmed to vary its brightness level repeatedly in an outwardly concentrically pattern to dynamically change the background luminance.

18. The apparatus of claim 16, wherein the camera device tracks movement of a marking device in front of the viewing screen; and the marking device is a laser pointer or a light pen.

19. The apparatus of claim 16, further comprising a central reference at the center of the visual grid and at least one peripheral reference.

* * * * *